United States Patent [19]
Osypka et al.

[11] Patent Number: 4,693,258
[45] Date of Patent: Sep. 15, 1987

[54] SURGICAL ELECTRODE FOR CARDIAC PACING AND MONITORING

[75] Inventors: Peter Osypka, Grenzach-Wyhlen; Hans Gerstmann, Lörrach, both of Fed. Rep. of Germany

[73] Assignee: Dr. Ing. P. Osypka GmbH Medizinelektronik, Grenzach-Wyhlen, Fed. Rep. of Germany

[21] Appl. No.: 805,978

[22] Filed: Dec. 5, 1985

[30] Foreign Application Priority Data

Dec. 11, 1984 [DE] Fed. Rep. of Germany ....... 3445102

[51] Int. Cl.$^4$ .............................................. A61B 5/04
[52] U.S. Cl. ................................. 128/783; 128/419 P; 128/642
[58] Field of Search ............... 128/639, 642, 783, 784, 128/785, 786, 419 P; 174/169, 188, 192

[56] References Cited

U.S. PATENT DOCUMENTS

| 3,434,091 | 4/1969 | Jerushalmi et al. | 128/419 P |
| 3,769,984 | 11/1973 | Meunch | 128/786 |
| 4,154,248 | 5/1979 | Jones | 128/419 P |
| 4,574,814 | 3/1986 | Buffet | 128/786 |

OTHER PUBLICATIONS

Deal et al., "Journal of Thoracic and Cardiovascular Surgery", vol. 55, No. 3, Mar. 1968, pp. 359-360.

Primary Examiner—William E. Kamm
Attorney, Agent, or Firm—Peter K. Kontler

[57] ABSTRACT

A surgical electrode wherein the terminal portion of a lead wire which extends from the thorax of a patient is connectable with a cardiac pacing or monitoring instrument by a rod-shaped electrically conductive male connector in cooperation with an insulating sleeve-like female connector which is slidable longitudinally of the male connector. The latter has a transverse slot or hole remote from one end of the male connector, and the terminal portion of the wire extends from the one end of the male connector, through the slot or hole, and back to the one end of the male connector. The female connector normally surrounds two legs of the terminal portion as well as the hole or that part of the slot which is nearer to the one end of the male connector but leaves the male connector exposed between that part of the wire which extends through the hole or slot and the other end of the male connector so that the exposed portion of the male connector can be inserted into the socket of a pacing or monitoring instrument. The female connector is movably connected with a tubular cover which can be caused to confine the exposed portion of the male connector when the latter is not attached to an instrument.

24 Claims, 10 Drawing Figures

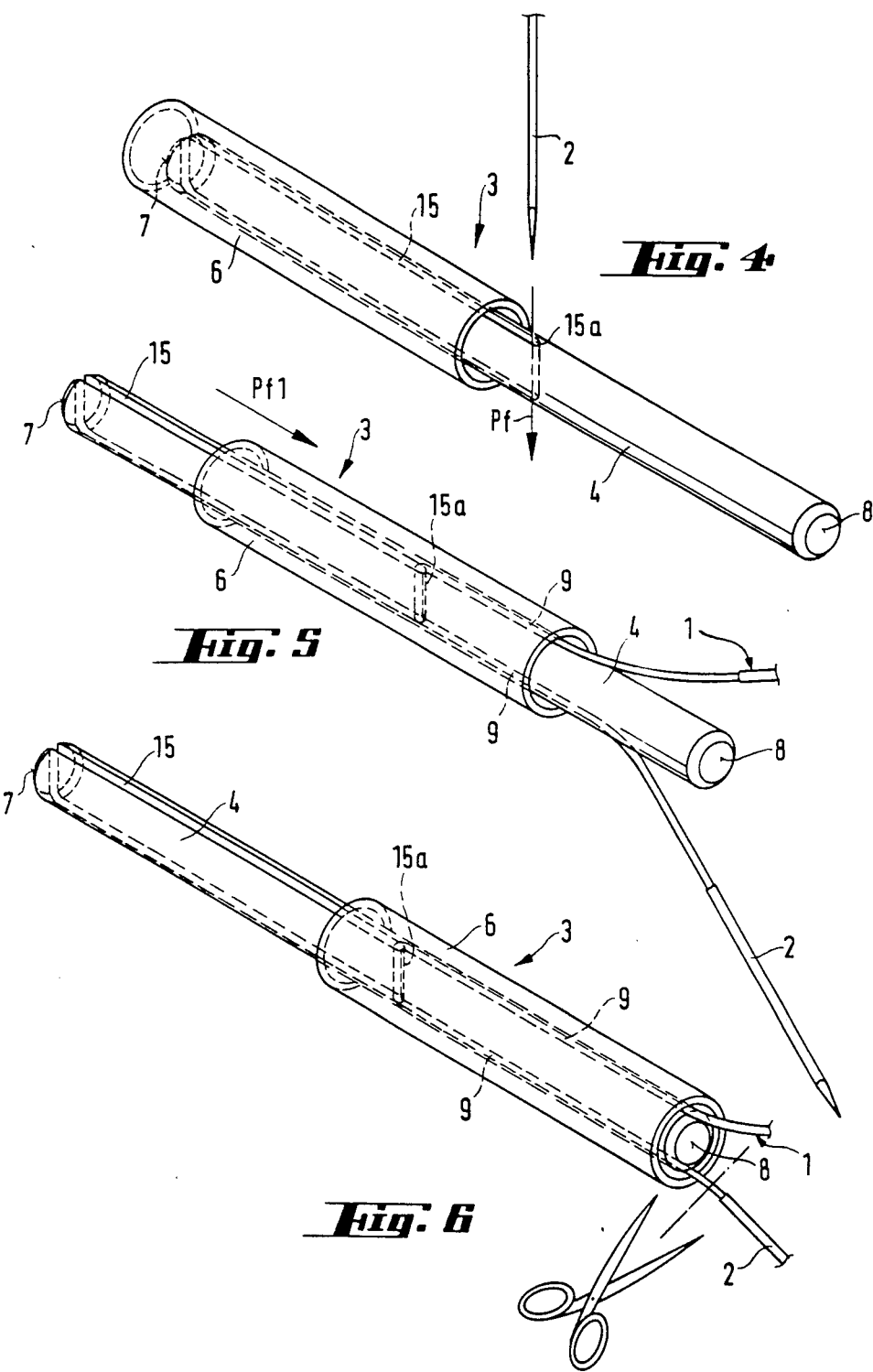

SURGICAL ELECTRODE FOR CARDIAC PACING AND MONITORING

BACKGROUND OF THE INVENTION

The present invention relates to surgical electrodes in general, and more particularly to improvements in surgical electrodes which can be implanted into the thorax of a patient to connect the heart with an external cardiac pacing or monitoring instrument. One end of a cardiac electrode is implanted into a patient's heart (e.g., in a manner as disclosed in the commonly owned copending patent applications Ser. Nos. 719,901 and 740,013 respectively filed Apr. 4 and May 31, 1985) and the other end (terminal portion) of the electrode extends from the thorax to be connected, or to be connectable, with an external pacemaker, an electrocardiograph or another medical instrument.

U.S. Pat. No. 4,010,756 discloses a heart pacer lead wire with a break-away needle. When the needle is broken away, the thus obtained plug must be connected with a cardiac pacer or with a cardiac monitoring instrument. As a rule, the instruments which are to be connected to a cardiac electrode have electrode clamping means or they utilize chucks which can receive and hold the exposed ends of the terminal portions of lead wires. The chucks are designed to receive plugs having a diameter in the range of two millimeters. Such plugs must be secured to the terminal portions of lead wires in a time-consuming manner. Known proposals include the utilization of specially designed clamps which serve as adapters between a plug and the terminal portion of the lead wire. Furthermore, it is still quite customary to utilize such relatively unreliable expedients as adhesive-coated tapes or bands in order to ensure that the terminal portion which extends from the thorax of a patient can be attached to the corresponding terminal of a medical instrument.

German Pat. No. 10 36 969 discloses a plug which can be used in laboratories and repair shops for electrical devices to establish a temporary connection between normally separated parts. The plug is rather bulky so that it cannot be used to connect the terminal portion of a lead wire with a cardiac pacing or monitoring instrument. There are additional reasons why such plug cannot be used in connection with cardiac electrodes even if its dimensions were reduced to the required size. Thus, the plug employs a male component having a transverse hole and a sleeve which is formed with two registering holes movable into register with the transverse hole for insertion of a wire through the sleeve and the male component. That portion of the wire which is caused to pass through the registering holes must be free of insulation in order to establish satisfactory electrical contact with the male component. The sleeve is then shifted axially to bend those portions of the wire which are immediately adjacent to the transverse hole. Blank portions of the wire are accessible at the exterior of the sleeve after the latter is moved to the operative position so that, were such plug used to connect the terminal portion of a lead wire with a medical instrument, the noninsulated portions of the wire would be likely to come into contact with the hands of nurses or other attendants to transmit undesirable electrical charges wire with attendant irregularity of heartbeat and danger to the life of the patient. An additional drawback of the patented plug is that it comprises a substantial number of parts including a spring which serves to bias the sleeve to a predetermined position.

U.S. Pat. No. 4,017,756 and German Offenlegungsschrift No. 28 46 136 disclose cardiac electrodes which employ needles and are provided with means for facilitating separation of the needles from the terminal portions of the lead wires so that the thus obtained plugs can be inserted into sockets. A drawback of such proposal is that the plug is extremely thin so that it does not fit into standard sockets. Furthermore, it is difficult to connect such plugs to extension cords or other types of adapters.

U.S. Pat. No. 4,442,840 discloses an electrical connector apparatus which employs a rather complex coupling consisting of synthetic plastic material. The construction of the coupling is such that the electrical connection between the terminal portion of the lead wire and the plug cannot be inspected except by taking the coupling apart. Furthermore, it is necessary to employ an extension cable which connects the terminal portion to the socket of a medical instrument.

OBJECTS AND SUMMARY OF THE INVENTION

An object of the invention is to provide a novel and improved surgical electrode which can be connected to or disconnected from a medical instrument in a simple and time-saving manner.

Another object of the invention is to provide the electrode with novel and improved assembly which can be used to electrically connect the terminal portion of the lead wire to the socket of a pacing or monitoring instrument.

A further object of the invention is to provide an electrode which need not employ a surgical needle so that the diameter of the needle can be reduced to a minimum.

An additional object of the invention is to provide a novel and improved method of connecting the terminal portion of a lead wire, which extends from the thorax of a patient, to the socket of a medical instrument.

Still another object of the invention is to provide an electrode which can be mass-produced at a reasonable cost.

An additional object of the invention is to provide an electrode which is constructed and assembled in such a way that the connection between discrete current conducting parts can be inspected at any time without any, even partial, dismantling of the electrode.

The invention resides in the provision of a surgical electrode which comprises a lead wire arranged to extend from the thorax of a patient for connection to a medical instrument, particularly for cardiac pacing or monitoring purposes. The lead wire has an elongated terminal portion, and the electrode further comprises an electrically conductive elongated male connector having first and second ends and a transversely extending passage which is remote from the first end. The terminal portion has a first leg which extends substantially longitudinally of the male connector, an intermediate part which extends through the passage, and a second leg which extends substantially longitudinally of the male connector. The electrode also comprises an electrically insulating female connector including an annular portion which clampingly surrounds the male connector and the two legs intermediate the passage and the first end of the male connector. The female connector is dimensioned and configured in such a way that at least a portion (hereinafter called plug) of the male connector between the intermediate part of the terminal portion of the lead wire and the second end of the male connector remains exposed. Such plug can be inserted into the socket of a cardiac pacemaker or into the socket of an instrument which monitors the heart of the patient. The annular portion of the female connector can constitute or form part of a sleeve, and the legs of the terminal portion preferably extend from the passage toward the first end of the male connector. Such annular portion is shiftable longitudinally of the male connector so that it can surround the plug in the region between the intermediate part of the terminal portion of the lead wire and the second end of the male connector and to thus expose the two legs of the terminal portion. The annular portion will assume such inoperative position preparatory to introduction of the terminal portion into the passage, e.g., with a surgical needle.

The passage can constitute a transverse recess (especially a hole or bore) which is remote from the second end of the male connector, and the intermediate part of the terminal portion is preferably nearer to the first than to the second end of the male connector (i.e., the plug is preferably longer than the remaining portion of the male connector).

The plug of the male connector is preferably rod-shaped and its diameter can approximate 2 mm. The preferably sleeve-like annular portion of the female connector can be slipped onto such plug so as to completely expose the two legs and the intermediate part of the terminal portion. The annular portion of the female connector is preferably made of a material which transmits light so as to allow for observation of the legs and intermediate part of the terminal portion when the annular portion of the female connector is held in the operative position. The entire female connector can be made of a transparent or translucent elastomeric synthetic plastic material. When in operative position, the annular portion of the female connector can surround a portion of or the entire passage, depending on the configuration and dimensions of the passage. The latter can constitute a slot which extends in the longitudinal direction of the male connector and can have an open end at the second end of the male connector, i.e., the plug can consist of two prongs which can resile toward and away from each other so as to be held in requisite frictional engagement with a socket which forms part of a cardiac pacing or monitoring instrument. If the passage is an elongated slot, that (closed) end of the slot which is nearest to the first end of the male connector receives the intermediate part of the terminal portion when the annular portion of the female connector is held in the operative position (in which the plug is exposed or in which the plug is not confined in the female connector). The annular portion preferably surrounds the closed end of the slot when the female connector is held in the operative position.

The electrode can further comprise a cover for temporary confinement of the plug so that the plug cannot accidentally contact an impulse-transmitting part or body when it is not inserted into a socket. Such electrode preferably further comprises means for movably connecting the cover to the female connector. The cover can include a tube which is movable relative to the connectors to and from an operative position in which the tube surrounds the plug. The connecting means can be integral with the cover and with the female connector and can include a flexible web, cord or strip. If the connecting means is relatively short, e.g., if the cover is closely or immediately adjacent to the female connector (as considered in the longitudinal direction of the male connector), and the cover includes a tube, the tube is preferably formed with an elongated slot so that it can be pivoted relative to the female connector between a first or operative position in which it confines the plug and a second or inoperative position in which the plug is exposed and can be inserted into a socket. The slot and the connecting means are preferably disposed at substantially diametrically opposite sides of the male connector, and the tube preferably includes an extension (serving as a handle) which projects beyond the second end of the male connector in the operative position of the tube so that it can be engaged by a finger or by a tool in order to pivot the tube toward the inoperative position (whereby the width of the slot increases and thereupon decreases).

The cover can include an unslotted tube which is connected with the female connector by an elongated web whose length at least matches the distance between the female connector (when the latter is held in the operative position) and the second end of the male connector so that the tube can be slipped onto and off the plug over the second end of the male connector. Such tube can have a closed end which is adjacent to the second end of the male connector when the tube conceals the plug.

The novel features which are considered as characteristic of the invention are set forth in particular in the appended claims. The improved electrode itself, however, both as to its construction and the mode of assembling the same, together with additional features and advantages thereof, will be best understood upon perusal of the following detailed description of certain specific embodiments with reference to the accompanying drawing.

BRIEF DESCRIPTION OF THE DRAWING

FIG. 4 is an enlarged perspective view of male and female connectors which form part of a second electrode, the female connector being slipped onto the normally exposed portion of the male connector to afford access to the closed end of an elongated slot in the male connector;

FIG. 5 illustrates the connectors of FIG. 4 in positions they assume subsequent to threading of the terminal portion of the lead wire through the closed end of the slot and with the female connector in an intermediate position;

FIG. 6 illustrates the structure of FIG. 5, with the female connector in its operative position in which a portion of the male connector is exposed for attachment to an instrument;

DESCRIPTION OF THE PREFERRED EMBODIMENTS

Figure 1:
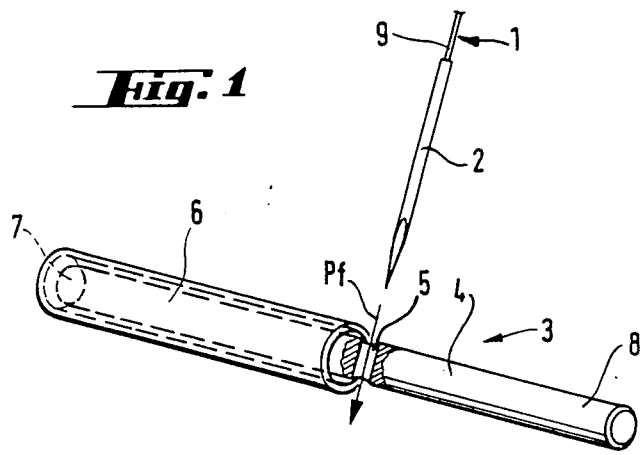
FIG. 1 is an enlarged perspective view of the male and female connectors of a surgical electrode which embodies one form of the invention, a portion of the male connector being broken away and the end of the terminal portion of the lead wire being connected to a needle for threading through the passage of the male connector.
Figure 2:
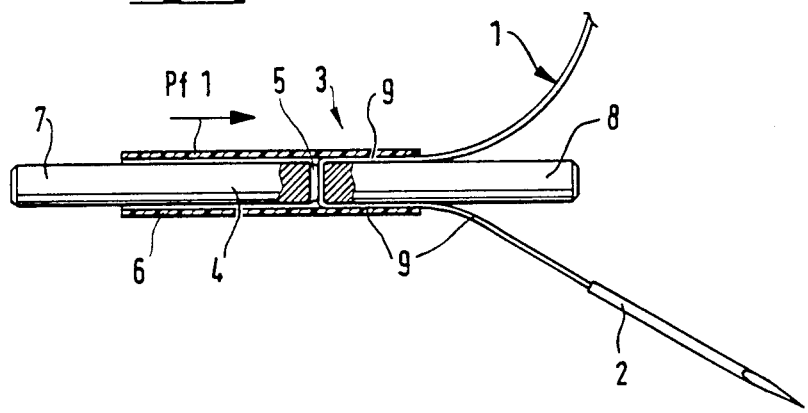
FIG. 2 is an elevational view of the electrode with the female connector shown in axial section and in an intermediate position in which it partially surrounds the two legs of the terminal portion.
Figure 3:
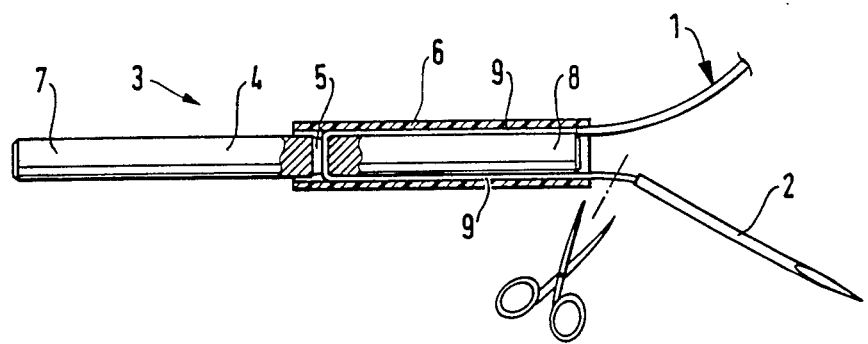
FIG. 3 illustrates the structure of FIG. 2 with the female connector in its operative position in which it confines the two legs and the intermediate part of the terminal portion of the lead wire and leaves an elongated portion of the male connector exposed for attachment to a medical instrument.

Referring first to FIGS. 1 to 3, there is shown a surgical electrode which comprises the terminal portion 1 of a lead wire that extends from the thorax of a patient and whose leader is connected with a surgical needle 2 prior to completed assembly of the electrode. The latter further comprises a connector assembly 3 including an elongated rod-shaped electrically conductive male connector 4 and an electrically insulating female connector in the form of an elongated cylindrical sleeve 6. The terminal portion 1 is surrounded by an insulator in the region of the surgical needle 2 which can also serve as a means for causing the lead wire to pass from the thorax, i.e., from the body of a patient whose heart must be temporarily connected to a pacemaker or to a cardiac monitoring instrument (such as an electrocardiograph).

The rod-shaped male connector 4 has first (right-hand) and second (left-hand) ends and a transverse passage 5 in the form of a hole or bore which is nearer to the first than to the second end, i.e., the rod-shaped portion 8 is shorter than the rod-shaped portion (plug) of the male connector 4. The length of the sleeve 6 (which is preferably made of a light-transmitting elastomeric synthetic plastic material) exceeds the length of the portion 8 so that, when the sleeve 6 is held in the operative position of FIG. 3, one of its end portions is flush with or even extends beyond the first end of the male connector 4 and its other endportion is located to the left of the passage 5, i.e., the latter is concealed in the interior of the annular intermediate portion of the sleeve.

The arrow Pf indicates the direction in which the needle 2 is caused to advance toward and through the passage 5 in order to move a length of the terminal portion 1 beyond the passage (see FIGS. 2 and 3). At such time, the sleeve 6 is held in the inoperative position of FIG. 1 in which it surrounds the plug 7 (and can extend beyond the second end of the male connector) but affords access to the passage 5. In the next step, the sleeve 6 is shifted axially in the direction of arrow Pf1 (FIG. 2) toward the operative position of FIG. 3 before the needle 2 is separated from the terminal portion 1 by shears (see FIG. 3) or by another suitable severing implement. The terminal portion 1 is then converted into a substantially U-shaped body having two legs 9 which extend longitudinally of the male connector 4 toward and beyond the first end of the male connector and an intermediate part which extends through the passage 5. The annular intermediate portion of the sleeve 6 clampingly surrounds the portion 8 of the male connector 4 and the two elongated legs 9 of the terminal portion 1. One leg 9 is connected to the major part of the lead wire, and the other leg 9 can terminate at the right-hand axial end of the sleeve 6, as viewed in FIG. 3. As mentioned above, the passage 5 is also confined in the sleeve 6 when the latter is held in the operative position of FIG. 3. At such time, the plug 7 of the male connector 4 is exposed and can be introduced into a socket. The legs 9 are biased against the external surface of the portion 8 and are conductively connected therewith so that the terminal portion 1 of the lead wire can receive impulses from or transmit impulses to the plug. The arrangement is preferably such that the terminal portion 1 is formed with two elongated legs 9 to ensure the establishment of a highly reliable electrical connection between the terminal portion and the plug 7. The feature that the terminal portion 1 is caused to change direction at both ends of the passage 5 (i.e., in the regions where the intermediate part of the terminal portion merges into the respective legs 9) also contributes to the establishment of a reliable electrical connection between the lead wire and the plug 7.

The dimensions of the sleeve 6 (prior to slipping it onto the male connector 4) and its material can be readily selected in such a way that the sleeve is in form-locking as well as in force-locking engagement with the legs 9 and urges the legs against the elongated portion 8 of the male connector 4. Nevertheless, the sleeve 6 can be shifted longitudinally of the male connector 4 for movement between the operative position of FIG. 3 (intermediate part and the legs 9 of the terminal portion 1 concealed) and the inoperative position of FIG. 1 in which the passage 5 is accessible to the needle 2. It is also within the purview of the invention to employ a shorter sleeve 6 so that the passage 5 is accessible when the sleeve is held in the operative position. The provision of a passage in the form of a dimetrically extending bore or hole 5 is preferred at this time because the surfaces surrounding the hole or bore ensure that the intermediate part of the terminal portion 1 (i.e., the part between the two legs 9) is held in a predetermined position and is urged against the surface surrounding the bore or hole as a result of axial movement of the sleeve 6 from the position of FIG. 1, through the intermediate position of FIG. 2, and to the position of FIG. 3.

Since the length of the plug 7 preferably exceeds the length of the other portion 8 of the male connector 4, the entire sleeve 6 can be shifted onto the plug 7 while the leader of the terminal portion 1 is threaded through the passage 5. When the sleeve 6 is held in the inoperative position of FIG. 1, its left-hand end may but need not extend beyond the respective (second) end of the male connector 4.

If the male connector 4 is a rod, or if the plug 7 is a rod, the diameter of the plug is preferably in the range of 2 mm. If the plug 7 is an elongated member having a polygonal cross-sectional outline, its maximum transverse dimension need not appreciably exceed 2 mm. As can be seen in FIGS. 1 to 3, the thickness of the terminal portion 1 is a minute fraction of the diameter of the plug 7, i.e., the diameter of the lead wire and of the needle 2 is, or can be, a minute fraction of one millimeter.

The hole or bore 5 can be replaced with a carefully finished passage which opens into the peripheral surface of the male connector 4 along an arc of 180 degrees. The provision of a passage in the form of a hole or bore is preferred at this time because such passage can more reliably confine the intermediate part of the terminal portion 1.

FIGS. 4 to 6 illustrate a modified electrode wherein the connector assembly 3 comprises an elongated rod-like male connector 4 whose passage is an elongated slot 15 extending longitudinally of the male connector and having a closed end 15a for the intermediate part of the lead wire and an open end in the region of the free end of the plug 7. The passage 15 performs the additional function of imparting to the plug 7 at least some resiliency by enabling the two elongated sections or tongues of the plug to move nearer to each other (especially in the region of the free end of the plug) during insertion of the plug into a socket and by thereupon tending to expand so as to maintain the plug in satisfactory contact with the socket.

The width of the slot 15 can be such that the intermediate part of the terminal portion 1 is actually clamped between the two inner end portions of the elongated sections or tongues constituting the plug 7 to thus ensure the establishment of a reliable electrical connection between the terminal portion 1 and the plug. FIG. 4 shows the sleeve 6 in the inoperative position, and FIG. 5 shows the sleeve 6 in an intermediate position during movement in the direction of arrow Pf1 toward the operative position of FIG. 6. In such operative position, the right-hand end of the sleeve 6 is close to or flush with the respective (first) end of the male connector 4. The terminal portion 1 of the lead wire is automatically converted into a U-shaped body with two elongated legs 9 and an intermediate part (in the closed end 15a of the slot 15) in response to movement of the sleeve 6 from the position of FIG. 4 to that which is shown in FIG. 6. The annular intermediate portion of the sleeve 6 then clampingly engages and surrounds the two legs 9 and urges them against the portion 8 of the male connector 4. At the same time, the sleeve 6 conceals the closed end 15a of the slot 15. The sleeve 6 subjects the legs 9 to tensional stresses while it moves from the position of FIG. 4 to the position of FIG. 6 so that the legs 9 pull the intermediate part of the terminal portion 1 against the surface bounding the closed end 15a of the slot 15; this also contributes to the establishment of a reliable electrical connection between the lead wire and the socket which receives the plug 7.

The length of the plug 7 exceeds the length of the remaining portion 8 of the male connector 4, and the length of the sleeve 6 is preferably less than or does not exceed the length of the plug 7 so that the entire sleeve can surround the plug and need not extend beyond the left-hand (second) end of the male connector 4 when the closed end 15a of the slot 15 is accessible to the needle 2. In other words, the sleeve 6 can be slipped onto the plug 7 before the needle 2 is caused to thread (arrow Pf) the terminal portion 1 of the lead wire transversely of and through the male connector 4 of the connector assembly 3. However, it is equally possible to introduce the terminal portion 1 through the open end of the slot 15 (at the free end of the plug 7) and to thereupon slide the sleeve 6 onto the plug 7 and toward the operative position of FIG. 6.

Figure 7:
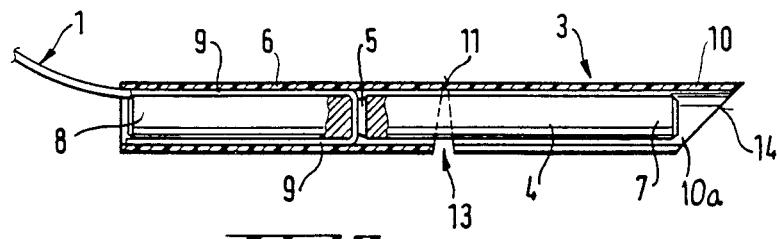
FIG. 7 is an enlarged partly elevational and partly axial sectional view of a third electrode wherein the female connector is integral with a cover having a slotted tube serving to confine the normally exposed portion of the male connector when the electrode is not attached to an instrument.
Figure 8:
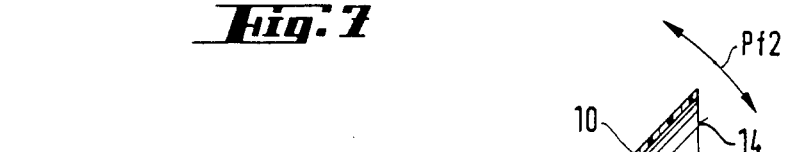
FIG. 8 illustrates the structure of FIG. 7 but with the tube pivoted to an inoperative position in which an elongated portion of the male connector is exposed.

FIGS. 7 and 8 illustrate an electrode whose connector assembly 3 includes a male connector 4 which is identical with or similar to the connector 4 of FIGS. 1–3, and a female connector or sleeve 6 which is integrally connected with a tubular cover 10 for temporary confinement of the plug 7 when the sleeve 6 is held in the operative position in which it clampingly engages and surrounds the portion 8 of the male connector 4 and the legs 9 of the terminal portion 1. The means for integrally connecting the sleeve 6 to the cover 10 includes a short web 11 which acts as a hinge and enables the cover to pivot (note the arrow Pf2) between the operative position of FIG. 7 (in which the plug 7 is concealed) and the inoperative position of FIG. 8 in which the plug 7 is exposed and can be inserted into a socket. In order to be capable of performing such pivotal movements, the cover 10 is formed with a longitudinally extending slot 10a. The slot 10a and the connecting means or hinge 11 are disposed at diametrically opposite sides of the male connector 4, and the cover 10 preferably comprises an extension 14 which projects beyond the second end of the male connector 4 (i.e., beyond the plug 7) and can be engaged by a tool or by a finger to pivot the cover between the operative and inoperative positions of FIGS. 7 and 8. At such time, the width of the slot 10a increases while the adjacent portions of the cover 10 slide along the plug 7 but the innate resiliency of the material of the cover suffices to ensure that the cover reassumes the shape of a tube in each of its two positions. The slot 10a is necessary because the connecting means 11 is relatively short, i.e., one end portion of the cover 10 is immediately adjacent to the respective end of the sleeve 6. The provision of an integral connection between the sleeve 6 and the cover 10 is desirable because it is much more difficult to misplace such parts and also because they can be manufactured (as a unit) at a reduced cost. The hinge 11 extends across the narrowest portion of a nearly annular clearance or gap 13 between the neighboring end portions of the cover 10 and sleeve 6. The extension 14 can be formed in a simple way by providing the cover 10 with an end face in a plane which is inclined with reference to the axis of the male connector 4. The longest part of the extension 14 is located substantially or exactly diametrically opposite the slot 10a.

The purpose of the cover 10 is to conceal the plug 7 when the latter is not inserted into a socket. This prevents accidental transmission of impulses to the patient's heart, e.g., by another person whose body is electrically charged in a manner such as to be harmful to the heart of the person whose thorax receives the lead wire. Such impulses could cause an undesirable and possibly dangerous stimulation of the heart which receives the other end of the lead wire.

Figure 9:
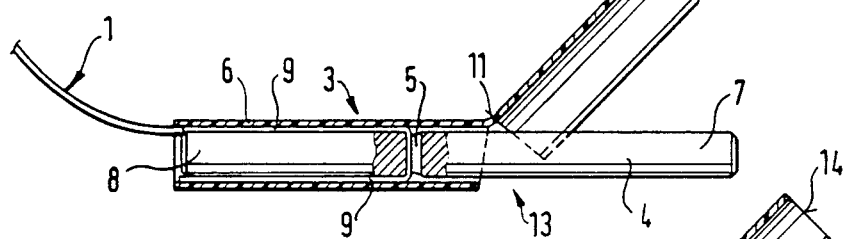
FIG. 9 is a partly elevational and partly axial sectional view of a fourth electrode wherein the cover includes an unslotted tube which is movably connected to the female connector by an elongated web of deformable material, the cover being shown in the inoperative position.
Figure 10:
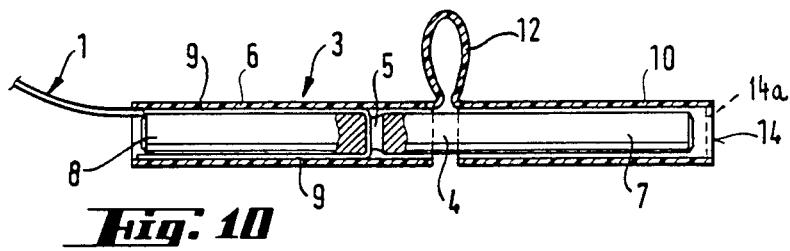
FIG. 10 illustrates the structure of FIG. 9 but with the cover in its operative position.

FIGS. 9 and 10 show a fourth electrode wherein the connector assembly 3 comprises a male connector 4 (identical with the male connector of FIGS. 1–3 and FIGS. 7–8) and a female connector or sleeve 6 which is integrally connected with a modified tubular cover 10 for the plug 7. The means for integrally connecting the sleeve 6 with the unslotted tubular cover 10 comprises an elongated rope, web or a like part 12 whose length preferably matches the distance between the right-hand end of the sleeve 6 (when the latter is held in the operative position of FIGS. 9–10) and the free end of the plug 7. This renders it possible to slip the tubular cover 10 onto and off the plug 7 over the respective (second) end of the male connector 4. The direction in which the cover 10 can be slipped onto the plug 7 is indicated by the arrow Pf3. When the cover 10 assumes the operative position of FIG. 10, the connecting means 12 forms a loop and thus allows the cover to move into close or immediate proximity of the adjacent end of the sleeve 6.

The end portion 14 of the cover 10 extends slightly beyond the free end of the plug 7 so as to further reduce the likelihood of accidental transmission of undesirable impulses to the terminal portion 1. If desired, the end portion 14 of the cover 10 can be closed by a transverse wall 14a (indicated in FIG. 10 by broken lines) so that the plug 7 is completely or practically completely confined when the cover assumes its operative position.

The cover 10 constitutes an optional but highly desirable and advantageous feature of the improved electrode. The pacemaker or a monitoring instrument is not permanently connected with the electrode so that the plug 7 is often withdrawn from its socket. At such time, the plug 7 could transmit impulses which would be harmful to the heart of the patient, and the cover 10 constitutes a very simple but highly effective and inexpensive means for preventing the transmission of such impulses. It has been found that the transmission of a current in the range of ten microamperes (such current can be readily transmitted by an attendant) suffices to endanger the life of a patient who relies on a cardiac pacer.

An important advantage of the improved electrode is that the terminal portion 1 of the lead wire can be connected directly with a plug 7 whose diameter is best suited for direct insertion into a standard socket. There is no need for extension cords or other types of adapters, and the means (sleeve 6) for connecting the terminal portion to the plug is simple and inexpensive and allows for convenient inspection of the legs 9 and intermediate part of the terminal portion 1 at any time because the material of the sleeve preferably transmits light. The sleeve 6 clamps the legs 9 to the portion 8 of the male connector 4 with a force which is amply sufficient to ensure the establishment of a reliable electrical connection without any shifting or slipping of the terminal portion 1 relative to the connector 4 and/or vice versa. The length of the uninsulated part of the terminal portion 1 need not exceed the combined length of the legs 9 and of the intermediate part in the passage 5 or 15 so that the leadwire cannot be brought into contact with impulse-transmitting bodies which could result in the transmission of unexpected, undesirable and dangerous stimuli to the heart of the patient. As mentioned above, the feature that the terminal portion 1 is flexed at several locations (where the intermediate part merges into the respective ends of the two legs 9) also contributes to reliable retention of the terminal portion in contact with the male connector 4. Experiments have proven the reliability of the improved electrode. The improved electrode does not employ any threaded parts which are necessary in certain heretofore known clamps for attachment of lead wires to medical instruments.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A surgical electrode comprising a lead wire arranged to extend from the thorax of a patient for connection to a medical instrument for cardiac pacing or monitoring purposes and having an elongated terminal portion; an electrically conductive elongated male connector having first and second ends and a transversely extending passage remote from said first end, said terminal portion having a first leg extending substantially longitudinally of said connector, an intermediate part in said passage and a second leg extending substantially longitudinally of said connector; and an electrically insulating female connector including an annular portion clampingly surrounding said male connector and said legs intermediate said passage and said first end, at least a portion of said male connector between said intermediate part and said second end being exposed.

2. The electrode of claim 1, wherein said annular portion is a sleeve and said legs extend from said passage toward the first end of said male connector.

3. The electrode of claim 1, wherein said annular portion is shiftable longitudinally of said male connector to surround the latter in the region between said intermediate part and said second end and to thereby expose the legs of said terminal portion.

4. The electrode of claim 1, wherein said passage is a recess which is remote from the second end of said male connector.

5. The electrode of claim 4, wherein said passage is a transverse hole.

6. The electrode of claim 1, wherein said intermediate part is nearer to said first end than to said second end.

7. The electrode of claim 1, wherein said portion of said male connector is rod-shaped and has a diameter of approximately 2 mm.

8. The electrode of claim 1, wherein said annular portion is slidable longitudinally of said male connector onto said portion of the male connector to thereby expose the legs and the intermediate part of said terminal portion.

9. The electrode of claim 1, wherein at least the annular portion of said female connector transmits light.

10. The electrode of claim 1, wherein at least the annular portion of said female connector consists of an elastomeric synthetic plastic material.

11. The electrode of claim 1, further comprising a removable cover for said portion of said male connector.

12. The electrode of claim 11, further comprising means for movably connecting said cover to said female connector.

13. The electrode of claim 12, wherein said cover includes a tube which is movable relative to said connectors to and from an operative position in which said tube surrounds said portion of said male connector.

14. The electrode of claim 12, wherein said connecting means is integral with said cover and with said female connector.

15. The electrode of claim 14, wherein said connecting means includes a flexible web.

16. The electrode of claim 12, wherein said cover includes a tube which is immediately adjacent to said female connector and has an elongated slot so as to permit such tube to be pivoted relative to said female connector between a first position in which said portion of said male connector is confined in said tube and a second position in which said portion of said male connector is exposed.

17. The electrode of claim 16, wherein said connecting means and said slot are disposed at substantially diametrically opposite sides of said male connector and said tube has an extension projecting beyond the second end of said male connector in the first position of said tube so that the tube can be pivoted between said positions through the medium of said extension.

18. The electrode of claim 12, wherein said cover includes a tube and said connecting means is an elongated deformable web whose length at least matches the distance between said female connector and the second end of said male connector so that said tube can be slipped onto and off said portion of said male connector over said second end while said annular portion surrounds the legs of said terminal portion and said male connector.

19. The electrode of claim 12, wherein said cover includes a tube movable to an operative position in which it surrounds said portion of said male connector and having a closed end which is adjacent to said second end in the operative position of said tube.

20. The electrode of claim 1, wherein said annular portion surrounds at least a portion of said passage.

21. The electrode of claim 1, wherein said passage is a slot which extends in the longitudinal direction of said male component.

22. The electrode of claim 21, wherein said slot extends all the way to the second end of said male component.

23. The electrode of claim 21, wherein said slot has a first end which is nearer to and a second end which is more distant from the first end of said male connector, said intermediate part of said terminal portion being disposed in the first end of said slot.

24. The electrode of claim 21, wherein said slot has a closed end and said annular portion surrounds the closed end of said slot.

* * * * *